United States Patent
Missel (10) Patent No.: US 12,340,532 B2
(45) Date of Patent: Jun. 24, 2025

(54) SYSTEM AND METHOD FOR OBTAINING PROFILE OF EYE LENS CAPSULE (71) Applicant: Alcon Inc., Fribourg (CH)

(72) Inventor: Paul J. Missel, Fort Worth, TX (US)

(73) Assignee: Alcon Inc., Fribourg (CH)

( * ) Notice: Subject to any disclaimer, the term of this patent is extended or adjusted under 35 U.S.C. 154(b) by 0 days.

(21) Appl. No.: 18/315,591

(22) Filed: May 11, 2023

(65) Prior Publication Data

US 2023/0281856 A1 Sep. 7, 2023

Related U.S. Application Data (63) Continuation of application No. 16/905,693, filed on Jun. 18, 2020, now Pat. No. 11,688,093.

(Continued)

(51) Int. Cl.
*A61B 3/00* (2006.01)
*A61B 3/10* (2006.01)
(Continued)

(52) U.S. Cl.
CPC .............. *G06T 7/62* (2017.01); *A61B 3/0025* (2013.01); *A61B 3/1005* (2013.01);
(Continued)

(58) Field of Classification Search
CPC ......... A61B 3/102; A61B 3/107; A61B 3/117; A61B 5/0066; A61B 3/0025; A61B 3/1173; A61B 3/1005; A61B 3/145; A61B 8/10; A61B 8/4209; A61B 8/0858; A61B 8/4218; A61B 8/4461; A61B 8/4483; A61B 3/10; A61B 3/135; A61B 8/13; A61B 8/40; A61B 8/4245; A61B 8/52; A61B 8/5223; A61B 8/5276; A61B 8/54; A61F 2009/00851;
(Continued)

(56) References Cited

U.S. PATENT DOCUMENTS 11,688,093 B2 * 6/2023 Missel ...................... G06T 3/00
382/128
2010/0179653 A1 7/2010 Argento
(Continued)

FOREIGN PATENT DOCUMENTS

CN 103501720 A 1/2014
CN 105517514 A 4/2016
(Continued)

*Primary Examiner* — Brandi N Thomas (57) ABSTRACT

A system includes a controller with at least one processor and at least one non-transitory, tangible memory on which instructions are recorded for executing a method for obtaining a profile of a lens capsule of an eye. The profile is represented by respective central surfaces and respective equatorial surfaces separated at respective transition points. The controller is configured to obtain imaging data for a portion of the lens capsule visible through a pupil of the eye. The imaging data is transformed to an adjusted frame of reference and fitted to the respective central surfaces in a predefined central region of the lens capsule. The profile is obtained based on a set of fitting parameters for the respective central and equatorial surfaces. The respective central surfaces and respective equatorial surfaces may be represented as elliptical cones and skewed parabolas, respectively.

6 Claims, 4 Drawing Sheets

Related U.S. Application Data (60) Provisional application No. 62/950,412, filed on Dec. 19, 2019.

(51) Int. Cl.
*A61B 3/117* (2006.01)
*A61B 3/14* (2006.01)
*A61F 2/16* (2006.01)
*A61F 9/007* (2006.01)
*G06T 3/00* (2006.01)
*G06T 7/62* (2017.01)

(52) U.S. Cl.
CPC ............ *A61B 3/1173* (2013.01); *A61B 3/145* (2013.01); *A61F 2/16* (2013.01); *A61F 9/007* (2013.01); *G06T 3/00* (2013.01); *G06T 2207/30041* (2013.01)

(58) Field of Classification Search
CPC .. A61F 2009/00882; A61F 2009/00887; A61F 9/008; A61F 9/00825; A61F 9/009; A61F 2/1613; A61F 2/16; A61F 2/1627; A61F 2/1648; A61F 2230/0063; A61F 2230/0067; A61F 9/007; A61F 2002/1681; A61F 2002/16965; A61F 2/1659; G06T 2207/10101; G06T 2207/30041; G06T 7/50; G06T 7/62; G06T 2207/10088; G06T 2207/10132; G06T 3/00; G06T 7/70

See application file for complete search history.

(56) References Cited

U.S. PATENT DOCUMENTS

2016/0302971 A1 10/2016 Morley
2017/0316571 A1* 11/2017 Martínez-Enríquez ..................... A61B 3/0025

FOREIGN PATENT DOCUMENTS

| | | |
|---|---|---|
| EP | 3491996 A1 | 6/2019 |
| JP | 2000069279 A | 3/2000 |
| JP | 2008531069 A | 8/2008 |
| JP | 2011509103 A | 3/2011 |
| JP | 2012521237 A | 9/2012 |
| JP | 2014231014 A | 12/2014 |
| JP | 2018508288 A | 3/2018 |
| WO | 2006053216 A2 | 5/2006 |
| WO | 2009080331 A1 | 7/2009 |
| WO | 2010109020 A1 | 9/2010 |
| WO | 2012134986 A1 | 10/2012 |
| WO | 2014172621 A2 | 10/2014 |
| WO | 2016142490 A1 | 9/2016 |
| WO | 2018021561 A1 | 2/2018 |

* cited by examiner

SYSTEM AND METHOD FOR OBTAINING PROFILE OF EYE LENS CAPSULE

TECHNICAL FIELD

The disclosure relates to a system and method for obtaining a profile of a lens capsule of an eye.

BACKGROUND

Humans have five basic senses: sight, hearing, smell, taste, and touch. Sight gives us the ability to visualize the world around us and connects us to our surroundings. Many people worldwide have issues with quality of vision and require the use of ophthalmic lenses, such as for example, intraocular lenses. The intraocular lens may be implanted into the eye in a cataract procedure to replace a human lens that has become cloudy. Having a profile of the lens capsule of the eye, prior to the procedure, assists in the selection of the intraocular lens.

SUMMARY

Disclosed herein is a system having a controller with at least one processor and at least one non-transitory, tangible memory on which instructions are recorded for executing a method for obtaining a profile of a lens capsule of an eye. Execution of the instructions by the processor causes the controller to obtain imaging data for a portion of the lens capsule visible through a pupil of the eye. The imaging data includes posterior datapoints and anterior datapoints and is transformed to an adjusted frame of reference having a first axis (X) and a second axis (Y). Also disclosed is a corresponding method for obtaining a profile of a lens capsule of an eye The profile is represented by respective central surfaces and respective equatorial surfaces separated by respective transition points. The controller is configured to fit the imaging data in the adjusted frame of reference to the respective central surfaces in a predefined central region of the lens capsule. The method includes obtaining a transition coordinate as a coordinate value of the respective transition points in a positive X-domain. The controller is configured to determine a set of fitting parameters for the respective central surfaces and the respective equatorial surfaces based on the transition coordinate and a plurality of constraints. The profile is obtained based on the set of fitting parameters for the respective central surfaces and the respective equatorial surfaces.

The controller may be configured to select an intraocular lens based at least partially on the profile of the lens capsule. Transforming the imaging data to the adjusted frame of reference includes fitting the posterior datapoints and the anterior datapoints to a first circle and a second circle, respectively, and determining intersection points of the first circle and the second circle. Transforming the imaging data to the adjusted frame of reference includes transforming the posterior datapoints and the anterior datapoints such that they are centered about a respective center of the intersection points and rotated such that a tilt angle of rotation is zero.

The controller is configured to fit the respective central surfaces in the adjusted frame of reference to respective conic equations for a conic surface. The controller is configured to determine a conic x-intercept as a coordinate on the first axis (X) where the respective conic equations intersect in a positive-x domain, the transition coordinate being a product of the conic x-intercept and a predefined constant, the predefined constant being less than 1.

The respective central surfaces include a central anterior surface. The controller may be configured to represent the central anterior surface as an elliptical cone characterized by a first plurality of variables (Ka, Qa, Ra), the first plurality of variables (Ka, Qa, Ra) being obtained by fitting the imaging data to the central anterior surface in the predefined central region in the adjusted frame of reference. The central anterior surface Ca(x) may be defined as:

$$Ca(x) = Ka - \frac{\sqrt{-(1+Qa)[(1+Qa)^2 x^2 - Ra^2]}}{(1+Qa)}.$$

The respective central surfaces include a central posterior surface. The controller may be configured to represent the central posterior surface as an elliptical cone characterized by a second plurality of variables (Kp, Qp, Rp), the second plurality of parameters (Kp, Qp, Rp) being obtained by fitting the imaging data to the central posterior surface in the predefined central region in the adjusted frame of reference. The central posterior surface Cp(x) may be defined as:

$$Cp(x) = Kp + \frac{\sqrt{-(1+Qp)[(1+Qp)^2 x^2 - Rp^2]}}{(1+Qp)}.$$

The set of fitting parameters include a first anterior parameter (Ga), a second anterior parameter (Pa), a first posterior parameter (Gp), a second posterior parameter (Pp) and respective coordinates (Xe, Ye) of a vertex in the adjusted frame of reference. The respective equatorial surfaces include an equatorial anterior surface and an equatorial posterior surface meeting at the vertex. The equatorial anterior surface and the equatorial posterior surface are represented by respective skewed parabola functions. The equatorial anterior surface is based in part on the first anterior parameter (Ga), the second anterior parameter (Pa) and the respective coordinates (Xe, Ye) of the vertex. The equatorial anterior surface Ea(x) may be defined as: Ea(x)=−[(1−Ga(Xe−x))][2√Pa(Xe−x)−Ye]. The equatorial posterior surface is based in part on the first posterior parameter (Gp), the second posterior parameter (Pp) and the respective coordinates (Xe, Ye) of the vertex. The equatorial posterior surface Ep(x) may be defined as: Ep(x)=+[(1−Gp(Xe−x))][2√Pp(Xe−x)+Ye].

The respective central surfaces include a central posterior surface and a central anterior surface. The respective equatorial surfaces include an equatorial anterior surface and an equatorial posterior surface. The plurality of constraints includes a first equation matching respective values of the central anterior surface and the equatorial anterior surface at the transition coordinate, and a second equation matching the respective values of the central posterior surface and the equatorial posterior surface at the transition coordinate.

The plurality of constraints includes a third equation matching respective first derivatives of the central anterior surface and the equatorial anterior surface at the transition coordinate, and a fourth equation matching the respective first derivatives of the central posterior surface and the equatorial posterior surface at the transition coordinate. The plurality of constraints includes a fifth equation matching respective second derivatives of the central anterior surface and the equatorial anterior surface at the transition coordinate, and a sixth equation matching the respective second derivatives of the central posterior surface and the equatorial posterior surface at the transition coordinate.

Disclosed herein is a system including a controller having at least one processor and at least one non-transitory, tangible memory on which instructions are recorded for executing a method for obtaining a profile of a lens capsule of an eye. The profile is represented by respective central surfaces and respective equatorial surfaces separated by respective transition points. Execution of the instructions by the processor causes the controller to obtain a lens diameter and at least two variables from a set of variables, the set of variables including a lens thickness, a central anterior apex and a central posterior apex. A transition coordinate is set as a product of the lens diameter and a predefined constant, the predefined constant being less than 0.5.

The controller is configured to obtain a first plurality of variables (Ka, Qa, Ra) and a pair of anterior parameters (Ga, Pa) by simultaneously solving a first group of constraints based in part on the transition coordinate. The controller is configured to obtain a second plurality of variables (Kp, Qp, Rp) and a pair of posterior parameters (Gp, Pp) by simultaneously solving a second group of constraints based in part on the transition coordinate.

The controller is configured to obtain the profile based on the first plurality of variables (Ka, Qa, Ra), the pair of anterior parameters (Ga, Pa), the second plurality of variables (Kp, Qp, Rp) and the pair of posterior parameter (Gp, Pp). An updated value of the lens diameter is obtained based on the profile, and an updated value of the transition coordinate is obtained based on the updated value of the lens diameter.

When a difference between the updated value of the transition coordinate and the transition coordinate is greater than a predefined threshold, the controller is configured to update the first plurality of variables (Ka, Qa, Ra) and the pair of anterior parameters (Ga, Pa) by simultaneously solving the first group of constraints based in part on the updated value of the transition coordinate. When the difference between the updated value of the transition coordinate and the transition coordinate is greater than the predefined threshold, the controller is configured to update the second plurality of variables (Kp, Qp, Rp) and the pair of posterior parameter (Gp, Pp) by simultaneously solving the second group of constraints based in part on the updated value of the transition coordinate.

The respective central surfaces include a central anterior surface and a central posterior surface, the respective equatorial surfaces including an equatorial anterior surface and an equatorial posterior surface. The controller is configured to represent the central anterior surface and the central posterior surface as respective elliptical cones characterized by the first plurality of variables (Ka, Qa, Ra) and the second plurality of variables (Kp, Qp, Rp), respectively. The controller is configured to represent the equatorial anterior surface and the equatorial posterior surface as respective skewed parabolas characterized by the pair of anterior parameters (Ga, Pa) and the pair of posterior parameters (Gp, Pp), respectively.

The first group of constraints includes: a first equation matching respective values of the central anterior surface and the equatorial anterior surface at the transition coordinate; a second equation matching respective first derivatives of the central anterior surface and the equatorial anterior surface at the transition coordinate; a third equation matching respective second derivatives of the central anterior surface and the equatorial anterior surface at the transition coordinate; and a fourth equation matching a respective coordinate of the central anterior surface to the central anterior apex.

The second group of constraints includes: a fifth equation matching the respective values of the central posterior surface and the equatorial posterior surface at the transition coordinate; a sixth equation matching respective first derivatives of the central posterior surface and the equatorial posterior surface at the transition coordinate; a seventh equation matching respective second derivatives of the central posterior surface and the equatorial posterior surface at the transition coordinate; and an eighth equation matching a respective coordinate of the central posterior surface to the central posterior apex.

The above features and advantages and other features and advantages of the present disclosure are readily apparent from the following detailed description of the best modes for carrying out the disclosure when taken in connection with the accompanying drawings.

DETAILED DESCRIPTION

Figure 1:
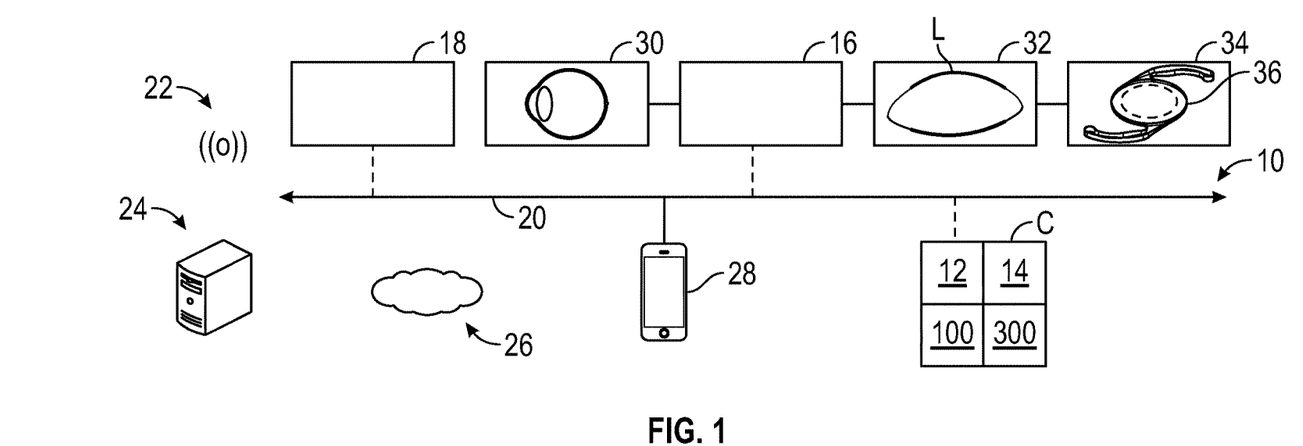
FIG. 1 is a schematic illustration of a system for obtaining a profile of a lens capsule of an eye, the system having a controller.

Referring to the drawings, wherein like reference numbers refer to like components, FIG. 1 schematically illustrates system 10 for obtaining a profile of a lens capsule of an eye. Referring to FIG. 1, the system 10 includes a controller C having at least one processor 12 and at least one memory 14 (or non-transitory, tangible computer readable storage medium) on which are recorded instructions for executing one or more methods. Method 100 and Method 300 are shown in and described below with reference to FIGS. 2 and 8, respectively.

Referring to FIG. 1, the system 10 may include a user interface 16 for collecting user data from one or more clinical facilities or electronic medical record units. The system 10 may include a data management unit 18 for storing and/or facilitating transfer of the user data and other functions. The various components of the system 10 may be configured to communicate via a short-range network 20 and/or a long-range network 22. Referring to FIG. 1, the controller C may be in communication with a remote server 24 and/or a cloud unit 26, which may include one or more servers hosted on the Internet to store, manage, and process data. The cloud unit 26 may be a private or public source of information maintained by an organization, such as for example, a research institute, a company, a university and/or a hospital.

Referring to FIG. 1, the short-range network 20 may be a bus implemented in various ways, such as for example, a serial communication bus in the form of a local area network. The local area network may include, but is not limited to, a Controller Area Network (CAN), a Controller Area Network with Flexible Data Rate (CAN-FD), Ethernet, blue tooth, WIFI and other forms of data connection. The long-range network 22 may be a Wireless Local Area Network (LAN) which links multiple devices using a wireless distribution method, a Wireless Metropolitan Area Networks (MAN) which connects several wireless LANs or a Wireless Wide Area Network (WAN) which covers large areas such as neighboring towns and cities. Other types of connections may be employed.

The controller C may be configured to receive and transmit wireless communication to the remote server 24 through a mobile application 28, shown in FIG. 1. The mobile application 28 may in communication with the controller C via the short-range network 20 such that it has access to the data in the controller C. In one example, the mobile application 28 is physically connected (e.g. wired) to the controller C. In another example, the mobile application 28 is embedded in the controller C. The circuitry and components of a remote server 24 and mobile application 28 ("apps") available to those skilled in the art may be employed.

Referring to FIG. 1, the user interface 16 and/or the controller C may be configured to communicate with an imaging device 30, which may be an optical coherence tomography machine. The imaging device 30 may be an ultrasound machine, a magnetic resonance imaging machine or other imaging device available to those skilled in the art. Additionally, the user interface 16 and/or the controller C may be in communication with a profile output module 32 and a lens selection module 34 for selecting an intraocular lens 36, as described below.

Figure 3:
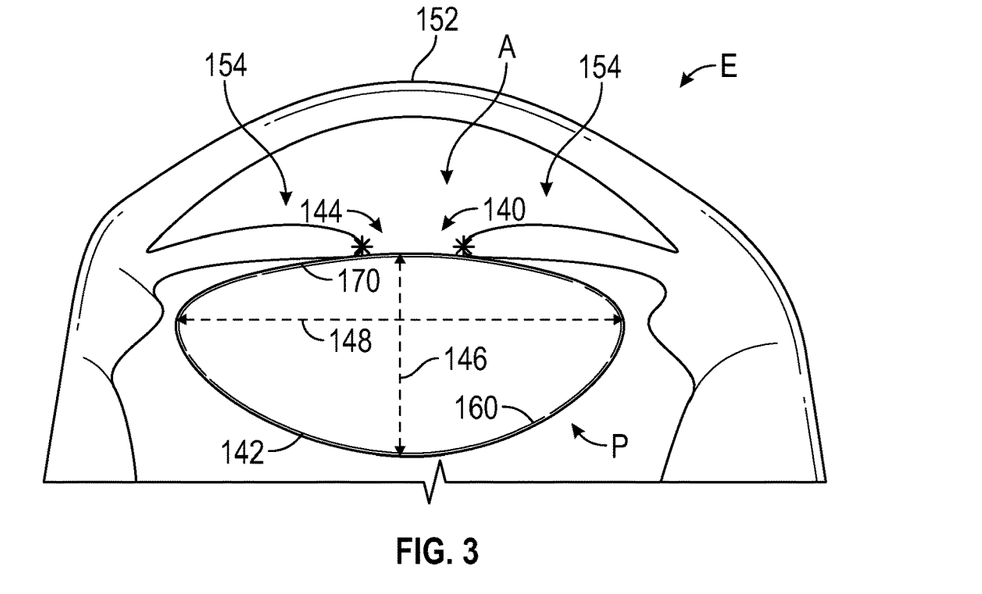
FIG. 3 is a schematic fragmentary example of a sectional image of an eye, the image having posterior datapoints and anterior datapoints of a lens capsule.

Referring to FIG. 3, an example image of an eye E is shown. As described below and referring to FIG. 3, the controller C is configured to obtain imaging data for a portion 140 of a lens capsule 142 visible through the pupil 144 of the eye E. The lens capsule 142 has a lens thickness 146 and a lens diameter 148. Also shown in FIG. 3 are the cornea 152 and iris 154. It is understood that FIG. 3 is not to scale.

Figure 2:
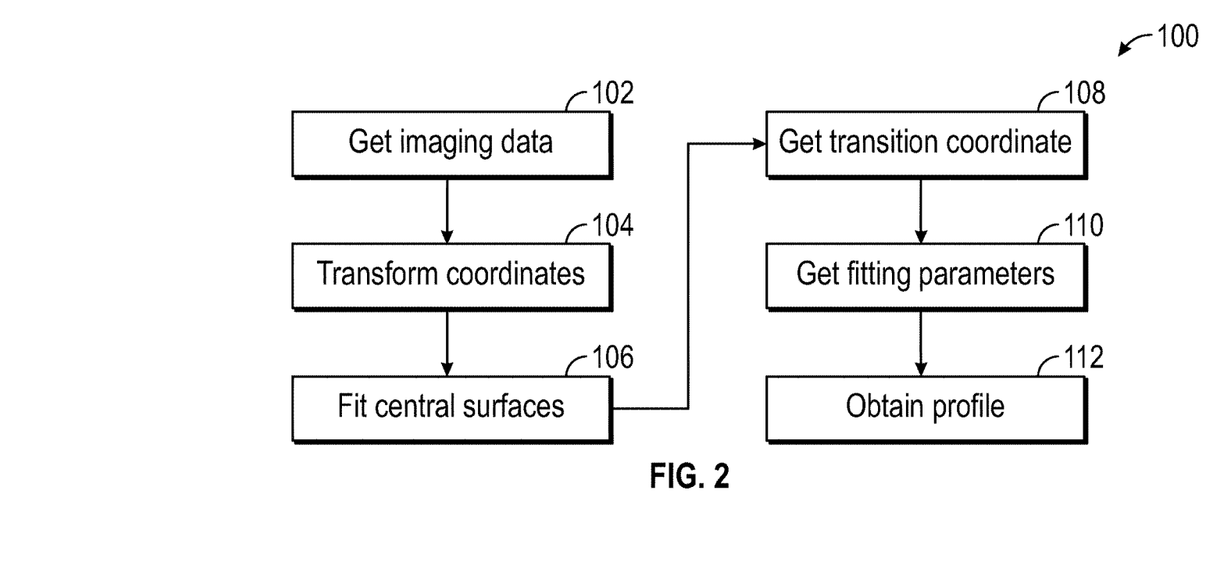
FIG. 2 is a schematic flowchart for a method executable by the controller of FIG. 1, in accordance with a first embodiment.

Referring now to FIG. 2, a flowchart of method 100 is shown. Method 100 need not be applied in the specific order recited herein and some blocks may be omitted. Per block 102 of FIG. 2, the method 100 includes obtaining imaging data for a portion 140 of the lens capsule 142 visible through the pupil 144 of the eye E. Method 100 enables a prediction of the entire shape of the lens capsule 142, including the portions of the shape that are obscured by the iris 154, using the portions 140 of the surface which is visible through the open pupil 144. The imaging data may be obtained via ultrasound bio-microscopy, optical coherence tomography, magnetic resonance imaging or any other imaging modality available to those skilled in the art. The imaging data may be derived from a single image or from multiple images. The imaging data may be obtained from imaging device 30.

Referring to FIG. 3, the imaging data includes posterior datapoints 160 (at a posterior side P) and anterior datapoints 170 (at an anterior side A). The posterior datapoints 160 and anterior datapoints 170 are shown plotted in FIG. 4 in pixel units (referred to herein as the original frame of reference 150), with a horizontal axis Q and a vertical axis R. The image shown in FIG. 4 (with posterior side P being above the anterior side A) is flipped vertically compared to FIG. 3 (with anterior side A being above the posterior side P) since the coordinate value in the vertical axis R advances going downwards in FIG. 3.

Figure 4:
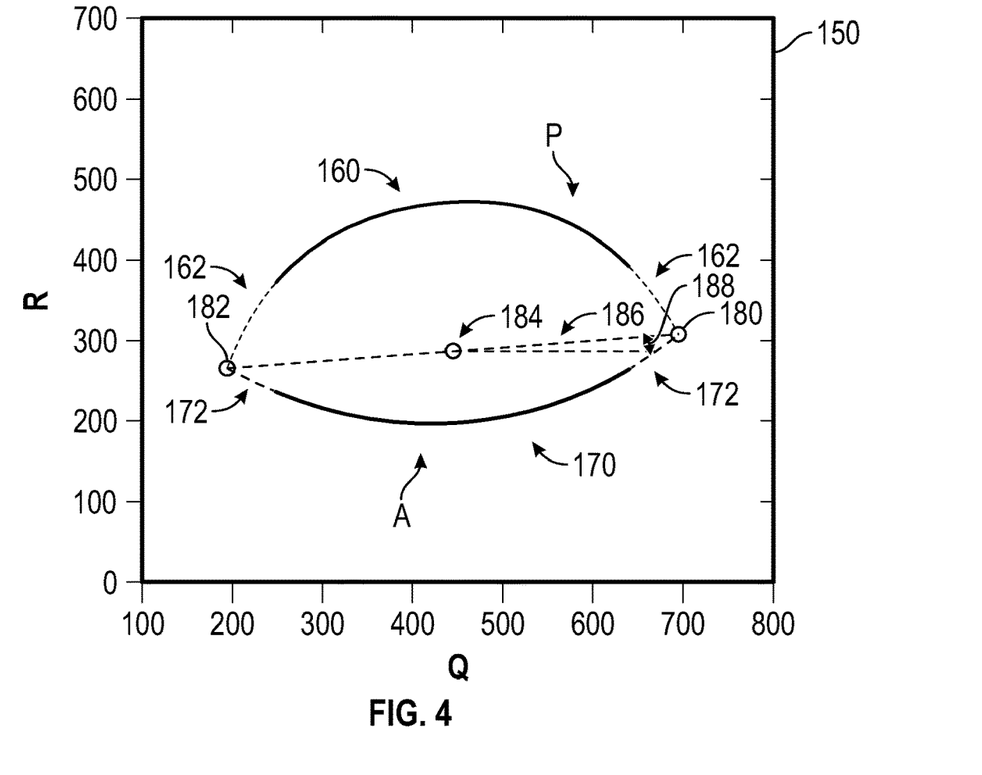
FIG. 4 is a schematic illustration of the posterior datapoints and anterior datapoints of FIG. 3, in an original frame of reference.
Figure 5:
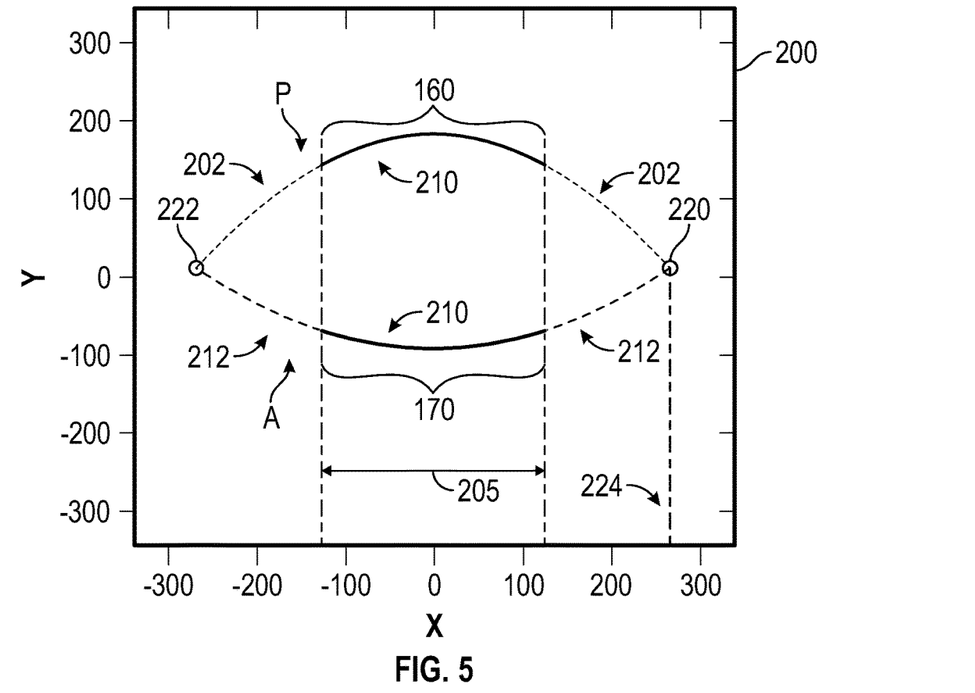
FIG. 5. is a schematic illustration of the posterior datapoints and anterior datapoints of FIG. 4, after transformation to an adjusted frame of reference.
Figure 6:
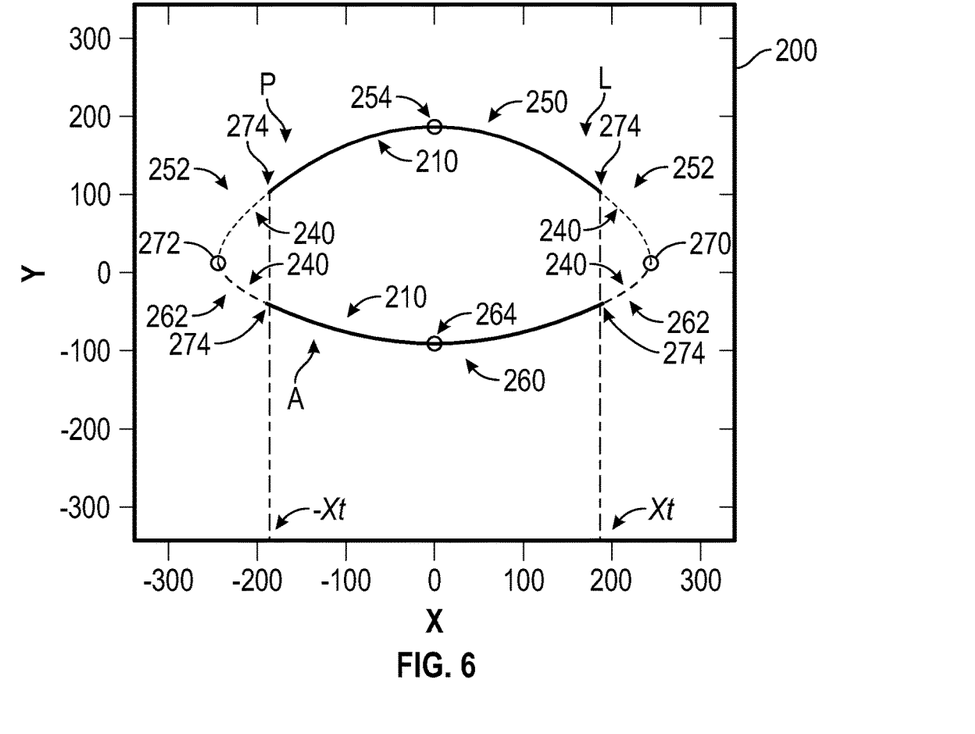
FIG. 6 is a schematic diagram of a profile of the lens capsule obtained by the system of FIG. 1, in the adjusted frame of reference.

Per block 104 of FIG. 2, the method 100 includes transforming the posterior datapoints 160 and anterior datapoints 170 from the original frame of reference 150 (shown in FIG. 4) to an adjusted frame of reference 200 (shown in FIGS. 5 and 6). First, referring to FIG. 4, the posterior datapoints 160 are fitted to the equation for a first circle 162 at the posterior side P. The anterior datapoints 170 are fitted to the equation for a second circle 172 at the anterior side A. The first circle 162 and the second circle 172 intersect at intersection points 180, 182, shown in FIG. 4.

Second, referring to FIG. 4, the controller C is configured to determine a center 184 between the intersection points 180, 182. The coordinate-transformed points (in the adjusted frame of reference 200 of FIG. 5) are obtained by centering the posterior datapoints 160 and the anterior datapoints 170 about the center 184 and rotating the centered coordinates by an angle exactly opposite to a tilt angle 188, such that the resulting tilt angle 188 becomes zero. The tilt angle 188 may be obtained as an arctangent of a ratio of the increase in the respective vertical coordinate value divided by an increase in the respective horizontal coordinate value between the intersection points 180, 182. The adjusted frame of reference 200 is shown in FIGS. 5-6 and has an X axis and a Y axis.

Per block 106 of FIG. 2 and referring to FIG. 5, the controller C is configured to fit the posterior datapoints 160 and the anterior datapoints 170 in the adjusted frame of reference 200 to respective central surfaces 210 (see FIG. 5) in a predefined central region 205 of the lens capsule 142. In one example, the predefined central region 205 is in a range 3-7 mm. In one example, the predefined central region 205 is about 5 mm, corresponding to an average-sized open pupil. The predefined central region 205 may be correlated to the opening diameter of the pupil 144 of a specific patient.

In the embodiment shown, the respective central surfaces 210 are elliptical cones. The respective central surfaces 210 may be other types of conic surfaces. It is understood that the form of the respective central surfaces 210 may be varied. Referring to FIG. 5, trace 202 and trace 212 show extrapolation of the respective central surfaces 210 at the posterior side P and the anterior side A, respectively. The respective central surfaces 210 are extrapolated to determine a positive conic intersection point 220 and a negative conic intersection point 222. The controller is configured to determine a conic x-intercept 224 as a coordinate on the X axis where the respective conic equations intersect in a positive-x domain. In other words, the conic x-intercept 224 is the X-coordinate of the positive conic intersection point 220.

Figure 7:
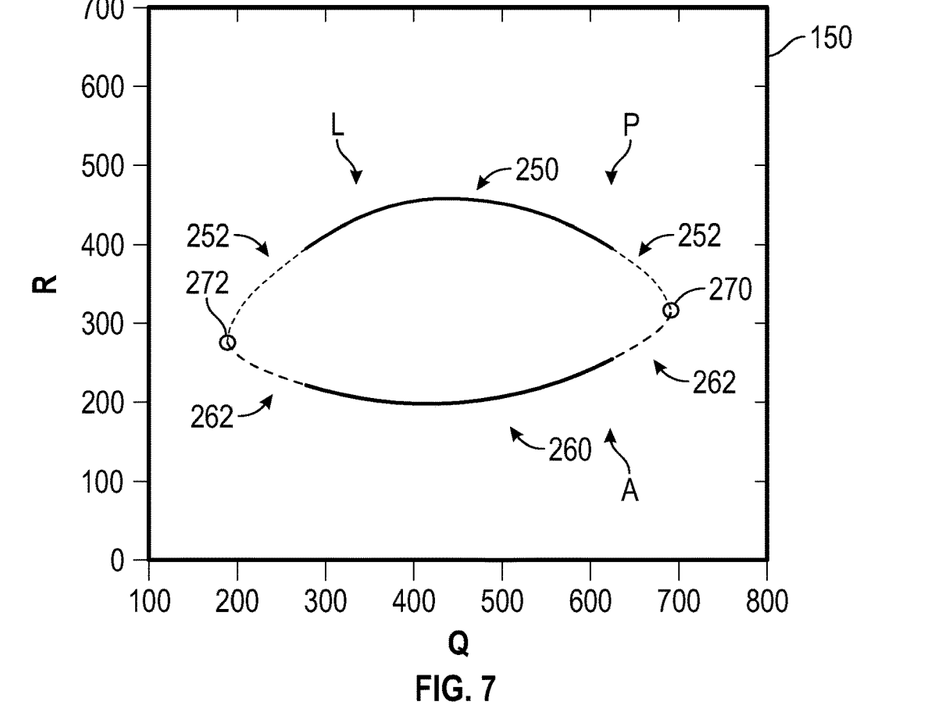
FIG. 7 is a schematic diagram of the profile of the lens capsule shown in FIG. 6, in the original frame of reference.

Referring to FIGS. 6-7, the profile L is represented by respective central surfaces 210 and respective equatorial surfaces 240. The respective equatorial surfaces 240 include equatorial posterior surfaces 252 and equatorial anterior surfaces 262. The central anterior surface 260 is flanked by the equatorial anterior surface 262 on either side. The central posterior surface 250 is flanked by the equatorial posterior surface 252 on either side. Referring to FIG. 6, the profile L of the lens capsule 142 is symmetric about the X-axis at X=0.

Per block 108 of FIG. 2, the controller C is configured to obtain a transition coordinate Xt (see FIG. 6) which is the coordinate value of the respective transition points 274 in a positive X-domain. Stated differently, the transition coordinate Xt is the positive coordinate on the X axis for the respective transition points 274. Referring to FIG. 6, the respective transition points 274 in the positive X-domain and the negative X-domain (corresponding to coordinate—Xt) are an equal distance from the X=0 line. The transition coordinate Xt is set as a product of the conic x-intercept 224 (Xi) and a predefined constant F, such that Xt=F*Xi. The predefined constant F is less than 1. In one example, the predefined constant F is within a range of 0.5 to 0.9. In one example, the predefined constant F is set to 0.7.

Referring to FIG. 6, the central posterior surface 250 and the central anterior surface 260 may be generated from expressions for the conic equations over the range −Xt<x<Xt, where Xt is the transition coordinate. In the example shown, the central anterior surface 260 is represented as an elliptical cone characterized by a first plurality of variables (Ka, Qa, Ra). The central anterior surface 260 or Ca(x) is defined as:

$$Ca(x) = Ka - \frac{\sqrt{-(1+Qa)\left[(1+Qa)^2 x^2 - Ra^2\right]}}{(1+Qa)}.$$

The first plurality of variables (Ka, Qa, Ra) are obtained by fitting the anterior datapoints 170 (in the adjusted frame of reference 200) in the predefined central region 205.

The central posterior surface 250 is represented as an elliptical cone characterized by a second plurality of variables (Kp, Qp, Rp). The central posterior surface 250 or Cp(x) is defined as:

$$Cp(x) = Kp + \frac{\sqrt{-(1+Qp)\left[(1+Qp)^2 x^2 - Rp^2\right]}}{(1+Qp)}.$$

The second plurality of parameters (Kp, Qp, Rp) being obtained by fitting the posterior datapoints 160 (in the adjusted frame of reference 200) in the predefined central region 205.

Referring to FIGS. 6-7, the equatorial posterior surfaces 252 and the equatorial anterior surfaces 262 may be represented by respective skewed parabola functions. The equatorial anterior surfaces 262 and the equatorial posterior surfaces 252 meet at a vertex 270 in the positive X-domain and another vertex 272 in the negative X-domain.

Per block 110 of FIG. 2, the method 100 includes determining a set of fitting parameters for the respective central surfaces 210 and the respective equatorial surfaces 240. The set of fitting parameters include a first anterior parameter (Ga), a second anterior parameter (Pa), a first posterior parameter (Gp), a second posterior parameter (Pp) and respective coordinates (Xe, Ye) of the vertex 270 in the positive X-domain in the adjusted frame of reference 200.

The equatorial posterior surface 252 (see FIGS. 6 and 7) is based in part on the first posterior parameter (Gp), the second posterior parameter (Pp) and the respective coordinates (Xe, Ye) of the vertex 270 in the positive X-domain. The equatorial posterior surface 252 or Ep(x) is defined as:

$Ep(x)=+[(1-Gp(Xe-x))][2\sqrt{Pp(Xe-x)}+Ye]$.

The equatorial anterior surface 262 (see FIGS. 6 and 7) based in part on the first anterior parameter (Ga), the second anterior parameter (Pa) and respective coordinates (Xe, Ye) of the vertex 270. The equatorial anterior surface 262 or Ea(x) is defined as:

$Ea(x)=-[(1-Ga(Xe-x))][2\sqrt{Pa(Xe-x)}-Ye]$.

The set of fitting parameters are based on the transition coordinate Xt and a plurality of constraints. The plurality of constraints includes first, second, third, fourth, fifth and sixth equations. In the example shown, there are six fitting parameters and six constraint equations. The six constraint equations may be solved numerically, for example, using the MATLAB function fsolve, employing the trust-region algorithm. Other numerical algorithms available to those skilled in the art may be employed.

The first equation matches respective values of the central anterior surface 260 and the equatorial anterior surface 262 at the transition coordinate Xt, as follows: Ca(Xt)=Ea(Xt). The second equation matches the respective values of the central posterior surface 250 and the equatorial posterior surface 252 at the transition coordinate Xt, as follows: Cp(Xt)=Ep(Xt).

The third equation matches respective first derivatives of the central anterior surface 260 and the equatorial anterior surface 262 at the transition coordinate Xt, as follows:

$$\frac{dCa(x)}{dx}\bigg|_{x=Xt} = \frac{dEa(x)}{dx}\bigg|_{x=Xt}.$$

The fourth equation matches the respective first derivatives of the central posterior surface 250 and the equatorial posterior surface 252 at the transition coordinate Xt, as follows:

$$\frac{dCp(x)}{dx}\bigg|_{x=Xt} = \frac{dEp(x)}{dx}\bigg|_{x=Xt}.$$

The fifth equation matches respective second derivatives of the central anterior surface 260 and the equatorial anterior surface 262 at the transition coordinate Xt, as follows:

$$\frac{d^2Ca(x)}{dx^2}\bigg|_{x=Xt} = \frac{d^2Ea(x)}{dx^2}\bigg|_{x=Xt}.$$

The sixth equation matches the respective second derivatives of the central posterior surface 250 and the equatorial posterior surface 252 at the transition coordinate Xt, as follows:

$$\frac{d^2Cp(x)}{dx^2}\bigg|_{x=Xt} = \frac{d^2Ep(x)}{dx^2}\bigg|_{x=Xt}.$$

Per block 112 of FIG. 2, the controller C is configured to obtain the profile L based on the set of fitting parameters (obtained in block 110) applied to the respective central surfaces 210 and the respective equatorial surfaces 240. FIG. 6 shows the profile L after the set of fitting parameters have been obtained. Additionally, per block 112, the profile L may be re-adjusted to the original frame of reference 150 shown in FIG. 4. FIG. 7 is a schematic diagram of the profile L after the opposite transformation from that of block 104, including de-centering and re-tilting. In order to provide visualization for clinicians, the profile L in the original frame of reference 150 may be superimposed onto the image of the eye E in FIG. 3.

Also, per block 112, the controller C may be configured to select an intraocular lens 36 based at least partially on the profile L of the lens capsule 142. Obtaining an accurate shape of the lens capsule L optimizes selection of the power of the intraocular lens 36. This effect is heightened where the intraocular lens 36 is an accommodative lens which may change its shape in response to external forces. In other words, the intraocular lens 36 may react differently to the same accommodative changes mediated by the ciliary muscles, depending on the geometric dimension and shape of the lens capsule 142.

Figure 8:
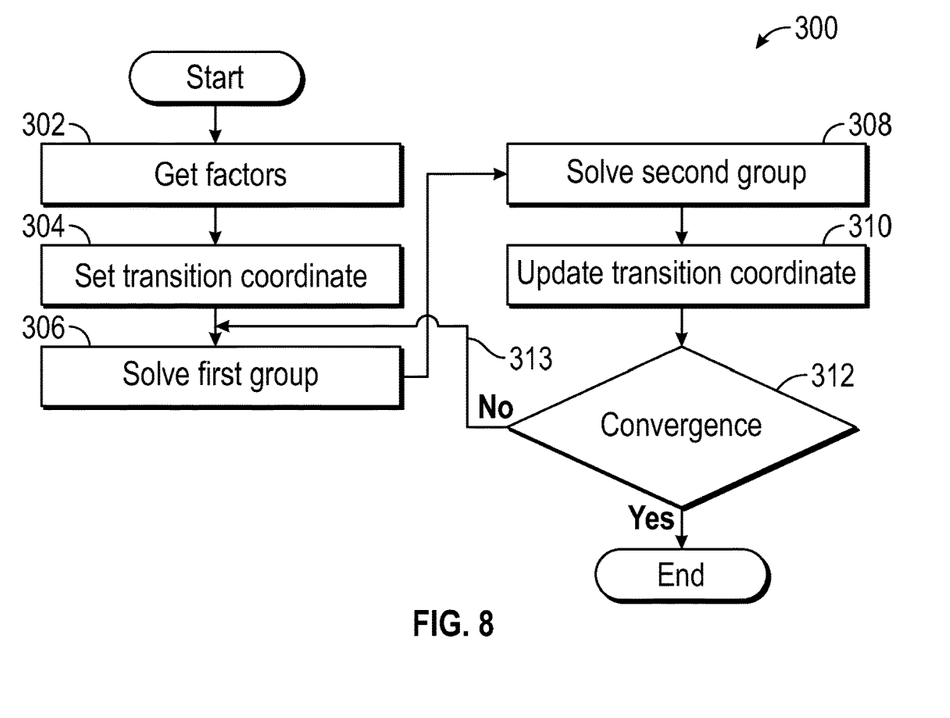
FIG. 8 is a schematic flowchart for a method executable by the controller of FIG. 1, in accordance with a second embodiment.

Referring now to FIG. 8, a flowchart of the method 300, executable by the controller C of FIG. 1, is shown. Method 300 need not be applied in the specific order recited herein and some blocks may be omitted. Per block 302 of FIG. 8, the controller C is configured to obtain a lens diameter 148 (see FIG. 3) and at least two variables from a set of variables. The set of variables includes a lens thickness 146 (see FIG. 3), respective coordinates on the Y-axis of the central anterior apex 264 (see FIG. 6) and the central posterior apex 254 (see FIG. 6). The set of variables may be obtained from the imaging device 30 of FIG. 1 or any other source. Method 300 enables a prediction of the entire shape of the lens capsule 142 using a handful of parameters.

Referring to FIG. 7, the method 300 includes representing the profile L with respective central surfaces 210 and respective equatorial surfaces 240 in the adjusted frame of reference 200, as shown in FIG. 6. The respective central surfaces 210 include a central anterior surface 260 and a central posterior surface 250, represented as elliptical cones characterized by a first plurality of variables (Ka, Qa, Ra) and a second plurality of variables (Kp, Qp, Rp), respectively. The respective equatorial surfaces 240 include an equatorial anterior surface 262 and an equatorial posterior surface 252, represented as skewed parabolas characterized by a pair of anterior parameters (Ga, Pa) and a pair of posterior parameters (Gp, Pp), respectively.

Per block 304 of FIG. 8, the controller C is configured to set the transition coordinate Xt (see FIG. 6) as a product of the lens diameter 148 (LD) and a predefined constant J, such that Xt=J*LD. The predefined constant J is less than 0.5. In one example, the predefined constant J is 0.35. The transition coordinate Xt may also be obtained as a product of the respective X-coordinate (Xe) of the vertex 270 in the positive X-domain and the predefined constant J, such that Xt=J*(2*Xe). The lens diameter 148 (LD) may be set as twice the value of the respective X-coordinate (Xe) of the vertex 270, LD=2*Xe.

Per block 306 of FIG. 8, the controller C is configured to obtain the first plurality of variables (Ka, Qa, Ra) and the pair of anterior parameters (Ga, Pa) by simultaneously solving a first group of constraints based in part on the transition coordinate Xt. The first group of constraints includes four equations which may be solved numerically, for example, using the MATLAB function fsolve. Since there are five unknowns and four equations, the Levenberg-Marquardt method may be used. Other numerical algorithms available to those skilled in the art may be employed.

The first equation matches respective values of the central anterior surface 260 and the equatorial anterior surface 262 at the transition coordinate Xt, as follows: Ca(Xt)=Ea(Xt). The second equation matches respective first derivatives of the central anterior surface 260 and the equatorial anterior surface 262 at the transition coordinate Xt, as follows:

$$\frac{dCa(x)}{dx}\bigg|_{x=Xt} = \frac{dEa(x)}{dx}\bigg|_{x=Xt}.$$

The third equation matches respective second derivatives of the central anterior surface 260 and the equatorial anterior surface 262 at the transition coordinate Xt, as follows:

$$\frac{dCp(x)}{dx}\bigg|_{x=Xt} = \frac{dEp(x)}{dx}\bigg|_{x=Xt}.$$

The fourth equation matches the respective coordinates (Y coordinate) of the central anterior surface 260 and the central anterior apex 264 (Yac) when the X coordinate is zero, such that Ca(0)=Yac.

Per block 308 of FIG. 8, the controller C is configured to obtain the second plurality of variables (Kp, Qp, Rp) and the pair of posterior parameter (Gp, Pp) by simultaneously solving a second group of constraints based in part on the transition coordinate Xt. The second group of constraints includes four equations (fifth through eighth equations) which may be solved numerically, for example, using the MATLAB function fsolve. Since there are five unknowns and four equations, the Levenberg-Marquardt method may be used. Other numerical algorithms available to those skilled in the art may be employed.

The fifth equation matches the respective values of the central posterior surface 250 and the equatorial posterior surface 252 at the transition coordinate Xt, as follows: Cp(Xt)=Ep(Xt). The sixth equation matches the respective first derivatives of the central posterior surface 250 and the equatorial posterior surface 252 at the transition coordinate Xt, as follows:

$$\frac{d^2Ca(x)}{dx^2}\bigg|_{x=Xt} = \frac{d^2Ea(x)}{dx^2}\bigg|_{x=Xt}.$$

The seventh equation matches the respective second derivatives of the central posterior surface 250 and the equatorial posterior surface 252 at the transition coordinate Xt, as follows:

$$\frac{d^2Cp(x)}{dx^2}\bigg|_{x=Xt} = \frac{d^2Ep(x)}{dx^2}\bigg|_{x=Xt}.$$

The eighth equation matches the respective coordinates (Y coordinate) of the central posterior surface 250 and the central posterior apex 254 (Ypc) when the X coordinate is zero, such that Cp (0)=Ypc. The central anterior apex 264 (Yac), central posterior apex 254 (Ypc) and the lens thickness 146 are related as follows: [Ypc=Yac+Lens Thickness].

The output of block 306 may be used to obtain the central anterior surface 260 and the equatorial anterior surface 262. The central anterior surface 260 or Ca(x) is defined as:

$$Ca(x) = Ka - \frac{\sqrt{-(1+Qa)\left[(1+Qa)^2 x^2 - Ra^2\right]}}{(1+Qa)}.$$

The equatorial anterior surface 262 or Ea(x) is defined as:
Ea(x)=−[(1−Ga(Xe−x))][2√(Pa(Xe−x))−Ye].

The output of block 308 may be used to obtain the central posterior surface 250 and the equatorial posterior surface 252. The central posterior surface 250 or Cp(x) is defined as:

$$Cp(x) = Kp + \frac{\sqrt{-(1+Qp)\left[(1+Qp)^2 x^2 - Rp^2\right]}}{(1+Qp)}.$$

The equatorial posterior surface 252 or Ep(x) is defined as: Ep(x)=+[(1−Gp(Xe−x))][2$\sqrt{Pp(Xe-x)}$+Ye].

Per block 310 of FIG. 8, the controller C is configured to obtain the profile L based on the first plurality of variables (Kp, Qp, Rp), the pair of anterior parameters (Ga, Pa), the second plurality of variables (Kp, Qp, Rp) and the pair of posterior parameter (Gp, Pp). The controller C is configured to obtain an updated value of the lens diameter 148 based on the profile L, and an updated value of the transition coordinate Xt based on the updated value of the lens diameter 148.

Per block 312 of FIG. 8, the controller C is configured to determine if a difference between the updated value of the transition coordinate and the transition coordinate is less than a predefined threshold, in other words, if the updated value of the transition coordinate and the transition coordinate converge to within the predefined threshold. If so, the method 300 is ended. The controller C may be configured to select an intraocular lens 36 based at least partially on the profile L of the lens capsule 142.

If not, as shown by line 313, the method 300 loops back to block 306 and the controller C is configured to update the first plurality of variables (Ka, Qa, Ra) and the pair of anterior parameters (Ga, Pa) by simultaneously solving the first group of constraints based in part on the updated value of the transition coordinate. Additionally, the controller C is configured to update the second plurality of variables (Kp, Qp, Rp) and the pair of posterior parameter (Gp, Pp) by simultaneously solving the second group of constraints based in part on the updated value of the transition coordinate.

In summary, the system 10 (via execution of the method 100 and/or method 300) enables the prediction of a profile L of the lens capsule 142 with relatively high accuracy while requiring a relatively small number of parameters. The system 10 uses separate parameter values for the anterior side A and the posterior side P of the lens capsule 142, thus capturing the physiologic asymmetric nature of the shape of the lens capsule 142, which can be flatter on one side compared to the other.

The controller C of FIG. 1 includes a computer-readable medium (also referred to as a processor-readable medium), including a non-transitory (e.g., tangible) medium that participates in providing data (e.g., instructions) that may be read by a computer (e.g., by a processor of a computer). Such a medium may take many forms, including, but not limited to, non-volatile media and volatile media. Non-volatile media may include, for example, optical or magnetic disks and other persistent memory. Volatile media may include, for example, dynamic random-access memory (DRAM), which may constitute a main memory. Such instructions may be transmitted by one or more transmission media, including coaxial cables, copper wire and fiber optics, including the wires that comprise a system bus coupled to a processor of a computer. Some forms of computer-readable media include, for example, a floppy disk, a flexible disk, hard disk, magnetic tape, other magnetic medium, a CD-ROM, DVD, other optical medium, punch cards, paper tape, other physical medium with patterns of holes, a RAM, a PROM, an EPROM, a FLASH-EEPROM, other memory chip or cartridge, or other medium from which a computer can read.

Look-up tables, databases, data repositories or other data stores described herein may include various kinds of mechanisms for storing, accessing, and retrieving various kinds of data, including a hierarchical database, a set of files in a file system, an application database in a proprietary format, a relational database management system (RDBMS), etc. Each such data store may be included within a computing device employing a computer operating system such as one of those mentioned above and may be accessed via a network in one or more of a variety of manners. A file system may be accessible from a computer operating system and may include files stored in various formats. An RDBMS may employ the Structured Query Language (SQL) in addition to a language for creating, storing, editing, and executing stored procedures, such as the PL/SQL language mentioned above.

The detailed description and the drawings or FIGS. are supportive and descriptive of the disclosure, but the scope of the disclosure is defined solely by the claims. While some of the best modes and other embodiments for carrying out the claimed disclosure have been described in detail, various alternative designs and embodiments exist for practicing the disclosure defined in the appended claims. Furthermore, the embodiments shown in the drawings or the characteristics of various embodiments mentioned in the present description are not necessarily to be understood as embodiments independent of each other. Rather, it is possible that each of the characteristics described in one of the examples of an embodiment can be combined with one or a plurality of other desired characteristics from other embodiments, resulting in other embodiments not described in words or by reference to the drawings. Accordingly, such other embodiments fall within the adjusted framework of the scope of the appended claims.

What is claimed is:

1. A system comprising:
    a controller having at least one processor and at least one non-transitory, tangible memory on which instructions are recorded for executing a method for obtaining a profile of a lens capsule of an eye;
    wherein the profile is represented by respective central surfaces and respective equatorial surfaces separated by respective transition points;
    wherein execution of the instructions by the processor causes the controller to:
        obtain a lens diameter and at least two variables from a set of variables, the set of variables including a lens thickness, a central anterior apex and a central posterior apex;
        set a transition coordinate as a product of the lens diameter and a predefined constant, the predefined constant being less than 0.5;
        obtain a first plurality of variables (Ka, Qa, Ra) and a pair of anterior parameters (Ga, Pa) by simultaneously solving a first group of constraints based in part on the transition coordinate; and
        obtain a second plurality of variables (Kp, Qp, Rp) and a pair of posterior parameters (Gp, Pp) by simultaneously solving a second group of constraints based in part on the transition coordinate.

2. The system of claim 1, wherein:
    the respective central surfaces include a central anterior surface and a central posterior surface, the respective equatorial surfaces including an equatorial anterior surface and an equatorial posterior surface;

the controller is configured to represent the central anterior surface and the central posterior surface as respective elliptical cones characterized by the first plurality of variables (Ka, Qa, Ra) and the second plurality of variables (Kp, Qp, Rp), respectively; and the controller is configured to represent the equatorial anterior surface and the equatorial posterior surface as respective skewed parabolas characterized by the pair of anterior parameters (Ga, Pa) and the pair of posterior parameters (Gp, Pp), respectively.

3. The system of claim 2, wherein:

the controller is configured to select an intraocular lens based at least partially on the profile of the lens capsule.

4. The system of claim 2, wherein the first group of constraints includes:

a first equation matching respective values of the central anterior surface and the equatorial anterior surface at the transition coordinate;

a second equation matching respective first derivatives of the central anterior surface and the equatorial anterior surface at the transition coordinate;

a third equation matching respective second derivatives of the central anterior surface and the equatorial anterior surface at the transition coordinate; and a fourth equation matching a respective coordinate of the central anterior surface to the central anterior apex.

5. The system of claim 2, wherein the second group of constraints includes:

a fifth equation matching the respective values of the central posterior surface and the equatorial posterior surface at the transition coordinate;

a sixth equation matching respective first derivatives of the central posterior surface and the equatorial posterior surface at the transition coordinate;

a seventh equation matching respective second derivatives of the central posterior surface and the equatorial posterior surface at the transition coordinate; and an eighth equation matching a respective coordinate of the central posterior surface to the central posterior apex.

6. The system of claim 2, wherein the controller is configured to:

obtain the profile based on the first plurality of variables (Ka, Qa, Ra), the pair of anterior parameters (Ga, Pa), the second plurality of variables (Kp, Qp, Rp) and the pair of posterior parameter (Gp, Pp);

obtain an updated value of the lens diameter based on the profile, and an updated value of the transition coordinate based on the updated value of the lens diameter; and when a difference between the updated value of the transition coordinate and the transition coordinate is greater than a predefined threshold, update the first plurality of variables (Ka, Qa, Ra) and the pair of anterior parameters (Ga, Pa) by simultaneously solving the first group of constraints based in part on the updated value of the transition coordinate; and when the difference between the updated value of the transition coordinate and the transition coordinate is greater than the predefined threshold, update the second plurality of variables (Kp, Qp, Rp) and the pair of posterior parameter (Gp, Pp) by simultaneously solving the second group of constraints based in part on the updated value of the transition coordinate.

* * * * *